US011844494B2

(12) United States Patent
Yu et al.

(10) Patent No.: US 11,844,494 B2
(45) Date of Patent: Dec. 19, 2023

(54) ALIGNMENT METHOD AND TOOLS

(71) Applicant: Boston Scientific Scimed, Inc., Maple Grove, MN (US)

(72) Inventors: Honggang Yu, San Jose, CA (US); Baocheng Yang, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 3 days.

(21) Appl. No.: 17/805,484

(22) Filed: Jun. 6, 2022

(65) Prior Publication Data

US 2022/0296299 A1 Sep. 22, 2022

Related U.S. Application Data

(63) Continuation of application No. 16/740,689, filed on Jan. 13, 2020, now Pat. No. 11,389,241.

(60) Provisional application No. 62/792,524, filed on Jan. 15, 2019.

(51) Int. Cl.
*A61B 18/22* (2006.01)
*G02B 6/26* (2006.01)
*G02B 27/10* (2006.01)
*H01S 3/00* (2006.01)
*A61B 18/20* (2006.01)

(52) U.S. Cl.
CPC .............. *A61B 18/22* (2013.01); *G02B 6/262* (2013.01); *G02B 27/106* (2013.01); *H01S 3/0071* (2013.01); *A61B 2018/20553* (2017.05)

(58) Field of Classification Search
CPC .. G02B 6/262; G02B 27/1006; G02B 27/106; H01S 3/0071; A61B 2018/20553; A61B 2018/00571; A61B 2018/2035; A61B 2018/20357; A61B 2018/20359; A61B 18/20

See application file for complete search history.

(56) References Cited

U.S. PATENT DOCUMENTS

| 4,590,598 A | 5/1986 | O'Harra, II |
| 4,601,037 A | 7/1986 | McDonald |
| 5,004,338 A * | 4/1991 | Morrow ................ G01J 1/0414 |
| | | 219/121.61 |

(Continued)

FOREIGN PATENT DOCUMENTS

| CN | 116086310 A * | 5/2023 |
| CN | 219048812 U * | 5/2023 |

(Continued)

*Primary Examiner* — Thomas A Hollweg
*Assistant Examiner* — Mary A El-Shammaa
(74) *Attorney, Agent, or Firm* — Seager, Tufte & Wickhem, LLP

(57) ABSTRACT

A laser system includes a first cavity to output a laser light along a first path, a first mirror to receive the laser light from the first cavity, and redirect the laser light along a second path that is different than the first path, a beam splitter removably located at a first position on the second path, a beam combiner removably located at a second position on the second path, and an alignment device having first and second alignment features. The first and second alignment features occupy the first position and the second position, respectively, on the second path, when the beam splitter and the beam combiner are removed from the first position and the second position.

20 Claims, 7 Drawing Sheets

(56) References Cited

U.S. PATENT DOCUMENTS

| | | | |
|---|---|---|---|
| 5,048,911 A | 9/1991 | Sang et al. | |
| 5,059,200 A | 10/1991 | Tulip | |
| 5,071,422 A | 12/1991 | Watson et al. | |
| 5,135,534 A | 8/1992 | Tulip | |
| 5,224,052 A * | 6/1993 | Hamar | G01B 11/272 700/192 |
| 5,269,778 A | 12/1993 | Rink et al. | |
| 5,304,167 A | 4/1994 | Freiberg | |
| 5,363,387 A | 11/1994 | Sinofsky | |
| 5,387,211 A | 2/1995 | Saadatmanesh et al. | |
| 5,689,520 A | 11/1997 | Hoang | |
| 5,798,518 A * | 8/1998 | Coleman | A61B 18/20 606/2 |
| 5,805,622 A | 9/1998 | Brinkmann | |
| 5,820,627 A | 10/1998 | Rosen et al. | |
| 5,860,972 A | 1/1999 | Hoang | |
| 5,873,875 A | 2/1999 | Altshuler | |
| 5,963,575 A | 10/1999 | Muller et al. | |
| 6,055,458 A | 4/2000 | Cochran et al. | |
| 6,080,148 A | 6/2000 | Damasco et al. | |
| 6,159,204 A | 12/2000 | Hibst | |
| 6,333,485 B1 | 12/2001 | Haight et al. | |
| 6,358,243 B1 | 3/2002 | Esterowitz et al. | |
| 6,554,825 B1 | 4/2003 | Murray et al. | |
| 6,761,713 B2 | 7/2004 | Teichmann | |
| 6,998,567 B2 | 2/2006 | Yeik | |
| 7,286,576 B2 | 10/2007 | Hollemann et al. | |
| 7,630,418 B2 | 12/2009 | Franjic et al. | |
| 7,630,420 B2 | 12/2009 | Boutoussov | |
| 7,649,153 B2 | 1/2010 | Haight et al. | |
| 7,846,191 B2 | 12/2010 | Vaynberg et al. | |
| 7,873,083 B2 | 1/2011 | Mordaunt et al. | |
| 7,957,440 B2 | 6/2011 | Boutoussov | |
| 7,970,030 B2 | 6/2011 | Rizoiu et al. | |
| 8,004,665 B2 | 8/2011 | Cooley | |
| 8,074,661 B2 | 12/2011 | Hutson et al. | |
| 8,083,731 B2 | 12/2011 | Tunnermann et al. | |
| 8,308,716 B2 | 11/2012 | Horvath | |
| 8,389,890 B2 | 3/2013 | Haight et al. | |
| 8,409,176 B2 | 4/2013 | Cecchetti et al. | |
| 8,574,224 B2 | 11/2013 | Shazly et al. | |
| 8,758,331 B2 | 6/2014 | Lubatschowski et al. | |
| 8,773,764 B2 | 7/2014 | Grapov et al. | |
| 8,804,779 B2 | 8/2014 | Mordaunt et al. | |
| 9,134,538 B1 * | 9/2015 | Augst | H01S 5/1007 |
| 9,254,536 B2 | 2/2016 | Hoff et al. | |
| 9,259,231 B2 | 2/2016 | Navve et al. | |
| 9,282,985 B2 | 3/2016 | Finkman et al. | |
| 9,486,286 B2 | 11/2016 | Hodel et al. | |
| 9,717,629 B2 | 8/2017 | Anderegg | |
| 9,757,199 B2 | 9/2017 | Chia et al. | |
| 9,895,196 B2 | 2/2018 | Waisman et al. | |
| 9,939,631 B2 | 4/2018 | Waisman et al. | |
| 9,968,403 B2 | 5/2018 | Hasenberg et al. | |
| 10,039,604 B2 | 8/2018 | Chia et al. | |
| 10,058,388 B2 | 8/2018 | Haight et al. | |
| 10,092,446 B2 | 10/2018 | Anderegg | |
| 10,096,963 B2 | 10/2018 | Lee | |
| 10,130,424 B2 | 11/2018 | Boutoussov et al. | |
| 10,135,216 B1 | 11/2018 | Brown | |
| 10,170,886 B2 | 1/2019 | Leonardo et al. | |
| 10,175,445 B2 | 1/2019 | Kraisler et al. | |
| 10,182,942 B2 | 1/2019 | Reich et al. | |
| 10,213,258 B2 | 2/2019 | Krupica | |
| 10,216,063 B2 | 2/2019 | Vasilyev et al. | |
| 10,231,781 B2 | 3/2019 | Waisman et al. | |
| 10,245,107 B2 | 4/2019 | Sierra et al. | |
| 10,256,598 B2 | 4/2019 | Myasnikov et al. | |
| 10,258,410 B2 | 4/2019 | Hiereth et al. | |
| 10,263,384 B2 | 4/2019 | Cannon et al. | |
| 10,277,001 B2 | 4/2019 | Marincek et al. | |
| 10,292,762 B2 | 5/2019 | Masansky | |
| 10,305,244 B2 | 5/2019 | Sierra et al. | |
| 10,383,690 B2 | 8/2019 | Hodel et al. | |
| 10,390,995 B2 | 8/2019 | Imeshev | |
| 2003/0109860 A1 | 6/2003 | Black | |
| 2005/0033388 A1 | 2/2005 | Brugger et al. | |
| 2006/0016790 A1 | 1/2006 | Yeik | |
| 2006/0142745 A1 | 6/2006 | Boutoussov | |
| 2007/0073279 A1 | 3/2007 | Rowe et al. | |
| 2007/0225696 A1 | 9/2007 | Davenport et al. | |
| 2007/0230520 A1 | 10/2007 | Mordaunt et al. | |
| 2007/0276359 A1 | 11/2007 | Segal | |
| 2008/0082085 A1 | 4/2008 | Krasutsky | |
| 2008/0234787 A1 | 9/2008 | Kaphan et al. | |
| 2009/0093868 A1 | 4/2009 | Kim et al. | |
| 2010/0165435 A1 | 7/2010 | Grapov et al. | |
| 2011/0125227 A1 | 5/2011 | Vaynberg et al. | |
| 2011/0125228 A1 | 5/2011 | Lytle et al. | |
| 2013/0211388 A1 | 8/2013 | Haight et al. | |
| 2014/0276669 A1 | 9/2014 | Imeshev | |
| 2014/0330258 A1 | 11/2014 | Iger | |
| 2014/0336626 A1 | 11/2014 | Jiang et al. | |
| 2015/0009576 A1 | 1/2015 | Mordaunt et al. | |
| 2015/0100048 A1 | 4/2015 | Hiereth et al. | |
| 2015/0230864 A1 | 8/2015 | Xuan et al. | |
| 2015/0272674 A1 | 10/2015 | Xuan et al. | |
| 2015/0285679 A1 * | 10/2015 | Kasiutsich | G01N 21/85 356/402 |
| 2015/0305811 A1 | 10/2015 | Neuberger | |
| 2015/0313672 A1 | 11/2015 | Milner et al. | |
| 2016/0111845 A1 | 4/2016 | Kraisler et al. | |
| 2016/0135894 A1 | 5/2016 | Finkman et al. | |
| 2016/0149370 A1 | 5/2016 | Marincek et al. | |
| 2016/0166319 A1 | 6/2016 | Yu et al. | |
| 2016/0166320 A1 | 6/2016 | Ciulla et al. | |
| 2016/0184019 A1 | 6/2016 | Griffin | |
| 2017/0027642 A1 | 2/2017 | Schuster | |
| 2017/0027644 A1 | 2/2017 | Hodel et al. | |
| 2017/0119577 A1 | 5/2017 | Imeshev | |
| 2017/0354465 A1 | 12/2017 | Rink et al. | |
| 2018/0034231 A1 | 2/2018 | Tagliaferri et al. | |
| 2018/0076593 A1 | 3/2018 | Lee | |
| 2018/0078418 A1 | 3/2018 | Berezhnyy et al. | |
| 2018/0092693 A1 | 4/2018 | Falkenstein et al. | |
| 2018/0109066 A1 | 4/2018 | Cannon et al. | |
| 2018/0147014 A1 | 5/2018 | Misra et al. | |
| 2018/0206918 A1 | 7/2018 | Waisman et al. | |
| 2018/0235699 A1 | 8/2018 | Hasenberg et al. | |
| 2018/0263643 A1 | 9/2018 | Shelton et al. | |
| 2018/0278006 A1 | 9/2018 | Moskalev et al. | |
| 2018/0289420 A1 | 10/2018 | Chalfant | |
| 2018/0303549 A1 | 10/2018 | Chia et al. | |
| 2018/0309915 A1 | 10/2018 | Takata | |
| 2018/0337507 A1 | 11/2018 | Peng et al. | |
| 2018/0344405 A1 | 12/2018 | Brown et al. | |
| 2018/0366896 A1 | 12/2018 | Yu | |
| 2018/0368671 A1 | 12/2018 | Nakayama | |
| 2018/0368915 A1 | 12/2018 | Xia et al. | |
| 2018/0369020 A1 | 12/2018 | Shacham et al. | |
| 2019/0007668 A1 | 1/2019 | Novotny et al. | |
| 2019/0015157 A1 | 1/2019 | Grace | |
| 2019/0015250 A1 | 1/2019 | Rathjen | |
| 2019/0041653 A1 | 2/2019 | Yeung et al. | |
| 2019/0058300 A1 | 2/2019 | Ferin et al. | |
| 2019/0064441 A1 | 2/2019 | Matsuda et al. | |
| 2019/0070429 A1 | 3/2019 | Marchesini et al. | |
| 2019/0072756 A1 | 3/2019 | Waisman et al. | |
| 2019/0076192 A1 | 3/2019 | Vilokkinen et al. | |
| 2019/0083308 A1 | 3/2019 | Rathjen | |
| 2019/0091806 A1 | 3/2019 | Dallarosa et al. | |
| 2019/0099612 A1 | 4/2019 | Hiereth et al. | |
| 2019/0101748 A1 | 4/2019 | Hiereth et al. | |
| 2019/0110845 A1 | 4/2019 | Yang | |
| 2019/0115712 A1 | 4/2019 | Lee, Jr. | |
| 2019/0142516 A1 | 5/2019 | Boutoussov et al. | |
| 2019/0146226 A1 | 5/2019 | Yu | |
| 2019/0146236 A1 * | 5/2019 | Hansen | G02B 27/145 359/489.08 |
| 2019/0159838 A1 | 5/2019 | Boutoussov et al. | |
| 2019/0163032 A1 | 5/2019 | Gapontsev et al. | |
| 2019/0175407 A1 | 6/2019 | Bacher et al. | |
| 2019/0183573 A1 | 6/2019 | Waisman et al. | |
| 2019/0192346 A1 | 6/2019 | Reich et al. | |

(56) References Cited

U.S. PATENT DOCUMENTS

| | | |
|---|---|---|
| 2019/0201100 A1 | 7/2019 | Brown et al. |
| 2019/0221989 A1 | 7/2019 | Sierra et al. |
| 2019/0223953 A1 | 7/2019 | Uusimaa et al. |
| 2019/0254746 A1 | 8/2019 | Block et al. |
| 2020/0222118 A1 | 7/2020 | Yu |
| 2021/0044072 A1* | 2/2021 | Yu ......................... H01S 5/4012 |
| 2022/0206239 A1* | 6/2022 | Yang ..................... H01S 3/0071 |
| 2022/0370129 A1* | 11/2022 | Yang ................ A61B 17/22004 |
| 2022/0376459 A1* | 11/2022 | Yang ..................... H01S 3/1305 |
| 2023/0130871 A1* | 4/2023 | Jung ...................... G02B 27/10 |
| | | 372/9 |

FOREIGN PATENT DOCUMENTS

| | | | |
|---|---|---|---|
| JP | H0521321 | 1/1993 | |
| WO | 02094088 | 11/2002 | |
| WO | WO-02094088 A2 * | 11/2002 | ............... A61B 3/12 |

* cited by examiner

ALIGNMENT METHOD AND TOOLS

CROSS-REFERENCE TO RELATED APPLICATIONS

This patent application is a continuation of U.S. Nonprovisional Patent Application No. 16/740,689, filed on Jan. 13, 2020, which claims the benefit of priority under 35 U.S.C. § 119 to U.S. Provisional Patent Application No. 62/792,524, filed Jan. 15, 2019, which are herein incorporated by reference in their its entireties.

TECHNICAL FIELD

The present disclosure relates generally to medical/surgical laser systems, and more particularly, to methods and tools for aligning the medical/surgical laser systems.

BACKGROUND

Medical laser systems are used for a variety of surgical procedures. These procedures may include dusting and/or fragmentation of stones in the kidney, the bladder, and/or the ureter. Medical laser systems are also used to create incisions and to ablate and/or coagulate soft tissues, such as, but not limited to, the prostate. Surgical lasers output from medical laser systems have small diameters, e.g., 2 μm, and are invisible to the naked eye. Thus, it is necessary to use a visible alignment laser beam to align the medical laser system.

Conventional alignment procedures for medical laser systems are time consuming, with alignment generally taking about one to two days to complete. One problem with conventional alignment techniques results from multiple beam spots showing on a mirror during the alignment. Big and weak alignment beam spots on the mirror make it difficult to provide accurate alignment results. Another problem associated with conventional alignment techniques is the inability to determine whether the alignment beam is perpendicular to the mirror surface. If the alignment beam is not perpendicular to the mirror surface, the output laser beam will not be in the same optical axis as the output fiber. The result is the failure of an output from a core fiber after the coarse alignment step at times, requiring additional manipulation of the medical laser system. Yet another problem associated with conventional alignment techniques is the use of a thermal paper during alignment. The use of thermal paper is necessary since the alignment is not accurate, and thermal paper aids in correcting this accuracy. When the output beam is shot through the thermal paper, however, particles are generated which can contaminate and cause damage to the optics.

SUMMARY OF THE DISCLOSURE

In one aspect, a laser system comprises: a first cavity configured to output a laser light along a first path; a first mirror configured to receive the laser light from the first cavity, and redirect the laser light along a second path that is different than the first path; a beam splitter removably located at a first position on the second path; a beam combiner removably located at a second position on the second path; and an alignment device having first and second alignment features, wherein the first and second alignment features are configured to occupy the first position and the second position, respectively, on the second path, when the beam splitter and the beam combiner are removed from the first position and the second position.

The alignment device may further include two extensions spaced apart from one another, wherein the first alignment feature may be a hole in one of the two extensions, and the second alignment feature may be a hole in another of the two extensions.

The alignment device may include a body portion having two slots, and each of the two extensions may extend at least partially through one of the two slots.

The first alignment feature may be equidistant from the body portion as the second alignment feature.

The laser system may further include one or more fastening components and may be configured to secure the beam splitter and the beam combiner into the first position and the second position, respectively, when the laser system is in an operating configuration, and may secure the alignment device so that the first alignment feature and the second alignment feature are in the first position and second position, respectively, when the laser system is in a first calibrating configuration.

The first mirror may be a Galvo mirror adjustable in at least two dimensions.

The laser system may further include a second mirror configured to direct laser energy from the first cavity to the first mirror along a third path that is different from the first path and the second path.

The second mirror may include a film applied to at least one surface of the second mirror.

The laser system may further include a second cavity configured to output a laser light along a fourth path, wherein the fourth path may be different than the first, second, and third paths.

The laser system may further include a third mirror configured to direct laser energy from the second cavity to the first mirror along a fifth path that is different from the fourth path.

The first cavity may include a fourth mirror, and the laser system may further include an alignment laser source, and a fiber may be configured to deliver an alignment laser light from the alignment laser source, through the first alignment feature and the second alignment feature, toward the fourth mirror.

The alignment laser light may be configured to travel through the second alignment feature before travelling through the first alignment feature.

The fiber may have a core diameter from 5 μm to 7 μm.

The fiber may have a numerical aperture from 0.11 to 0.13.

The alignment laser light may be configured to be directed from the first mirror to the fourth mirror.

According to another aspect, a method for aligning a laser system comprises: delivering an alignment beam, through a first alignment feature positioned at a first location and through a second alignment feature positioned at a second location, onto a first mirror contained within a first laser cavity; removing the first alignment feature and the second alignment feature from the laser system; and positioning a beam splitter at the first location, and a beam combiner at the second location.

The first alignment feature and the second alignment feature may both holes positioned within spaced apart extensions of an alignment device.

The laser system may include an adjustable mirror configured to redirect laser light from the first laser cavity, and the method further includes adjusting one or more angles of the adjustable mirror until the alignment beam is centered on the first mirror.

In yet another aspect, a method for aligning a laser system having a first laser cavity comprises: activating a first laser cavity to emit a laser light along a first path toward a first mirror; diverting the emitted light along a second path from the first mirror to a second mirror, wherein the second path is different than the first path; diverting the emitted light along a third path from the second mirror through a first output fiber; measuring a first power of the emitted laser light, at the first output fiber; measuring a second power of a reflection of the emitted laser light between a beam splitter and a beam combiner; determining whether a ratio of the first power to the second power is below a first threshold; and adjusting positions of the first mirror and/or the second mirror until a ratio of the first power to the second power is below a first threshold, while the first output fiber is coupled to the laser system.

The method may further include replacing the first output fiber with a second output fiber having one or more different optical properties than the first output fiber, activating the first laser cavity to emit the laser light along the first path toward the first mirror, diverting the emitted light along the second path from the first mirror to the second mirror, diverting the emitted light along the third path from the second mirror through the second output fiber, measuring the first power of the emitted laser light, at the second output fiber, measuring a third power of the reflection of the emitted laser light, between the beam splitter and the beam combiner, and adjusting positions of the first mirror and/or the second mirror until the ratio of the first power to the second power is below the first threshold, while the second output fiber is coupled to the laser system.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Figure 1:
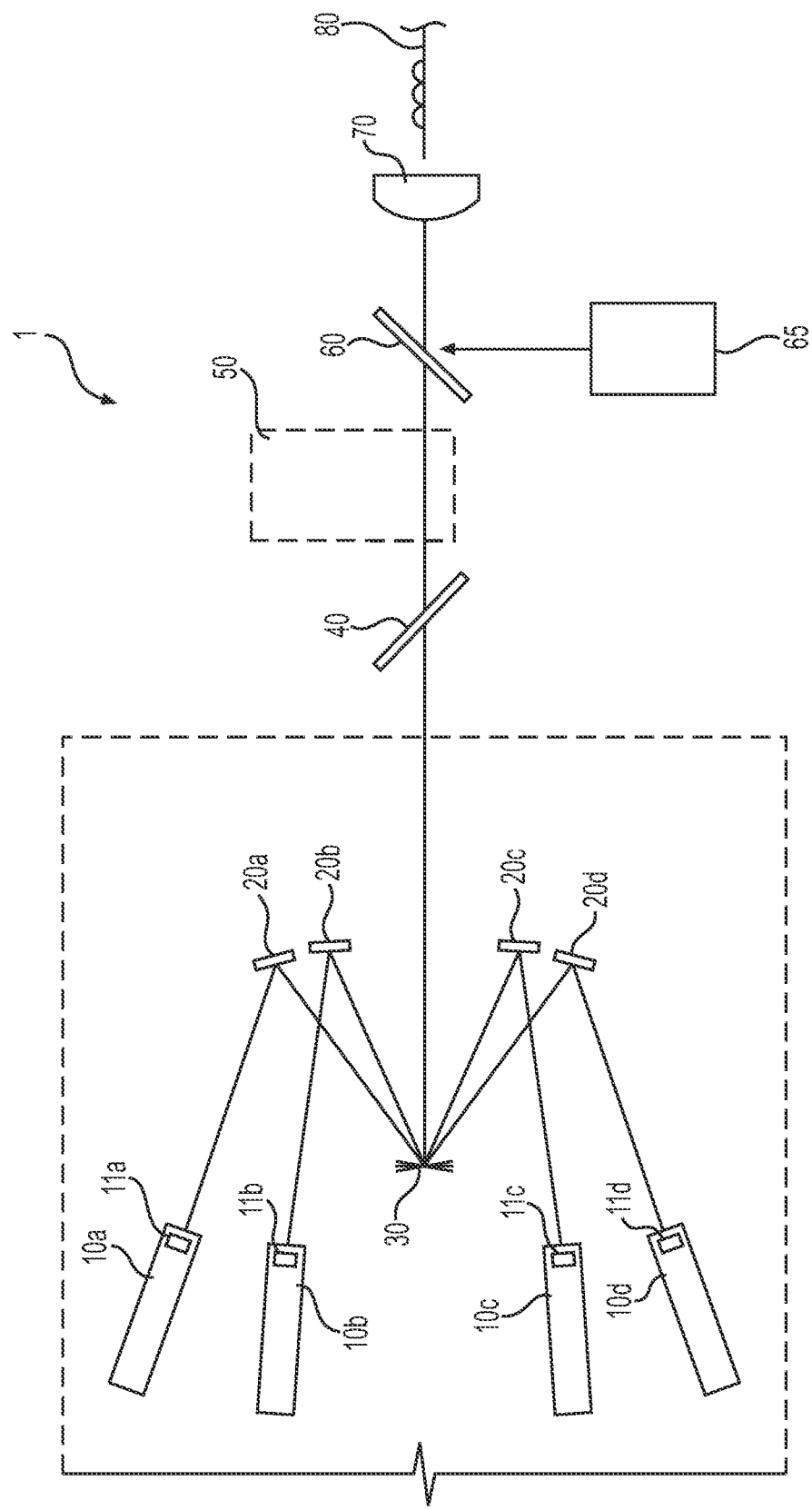
FIG. 1 is a schematic of a medical laser system according to an exemplary embodiment.

FIG. 1 illustrates an exemplary embodiment of a medical laser system 1. The medical laser system 1 includes one or more cavities 10a-10d, each cavity capable of outputting an output laser beam (or laser light). The output laser beam from each of the cavities 10a-10d is directed to a corresponding relay (e.g., first) mirror 20a-20d. For example, the output laser beam is output from cavity 10a to mirror 20a; for each cavity 10b to mirror 20b; from cavity 10c to 20c; and from cavity 10d to 20d. Each output laser beam is reflected from a respective one of the relay mirrors 20a-20d to a Galvo (e.g., second) mirror 30. For example, an output laser beam is reflected from relay mirror 20a to Galvo mirror 30. The Galvo mirror 30 reflects each output laser beam along a same optical path to a beam splitter 40, a safety shutter 50 (e.g., a shutter), and a beam combiner 60. The beam combiner 60 combines the output laser beams from the one or more cavities 10a-10d with an aiming beam from an aiming beam source 65, and passes the combined output laser beam to a coupling lens 70. The aiming beam may be a relatively low power light beam in the visual spectrum that enables an operator to visualize where the output beams from cavities 10a-10d will be fired. The coupling lens 70 couples the output laser beam and matches the output laser beam to the output fiber 80, to be transmitted to a delivery location.

To help ensure proper output and to help avoid damage to the medical laser system 1, and injuries to the user and/or the patient, the medical laser system 1 may be calibrated prior to use. The calibration and alignment of the medical laser system 1 may help ensure that the output laser from the one or more cavities 10a-10d properly reflects off each mirror and are coupled through coupling lens 70 into the output fiber 80.

Figure 2:
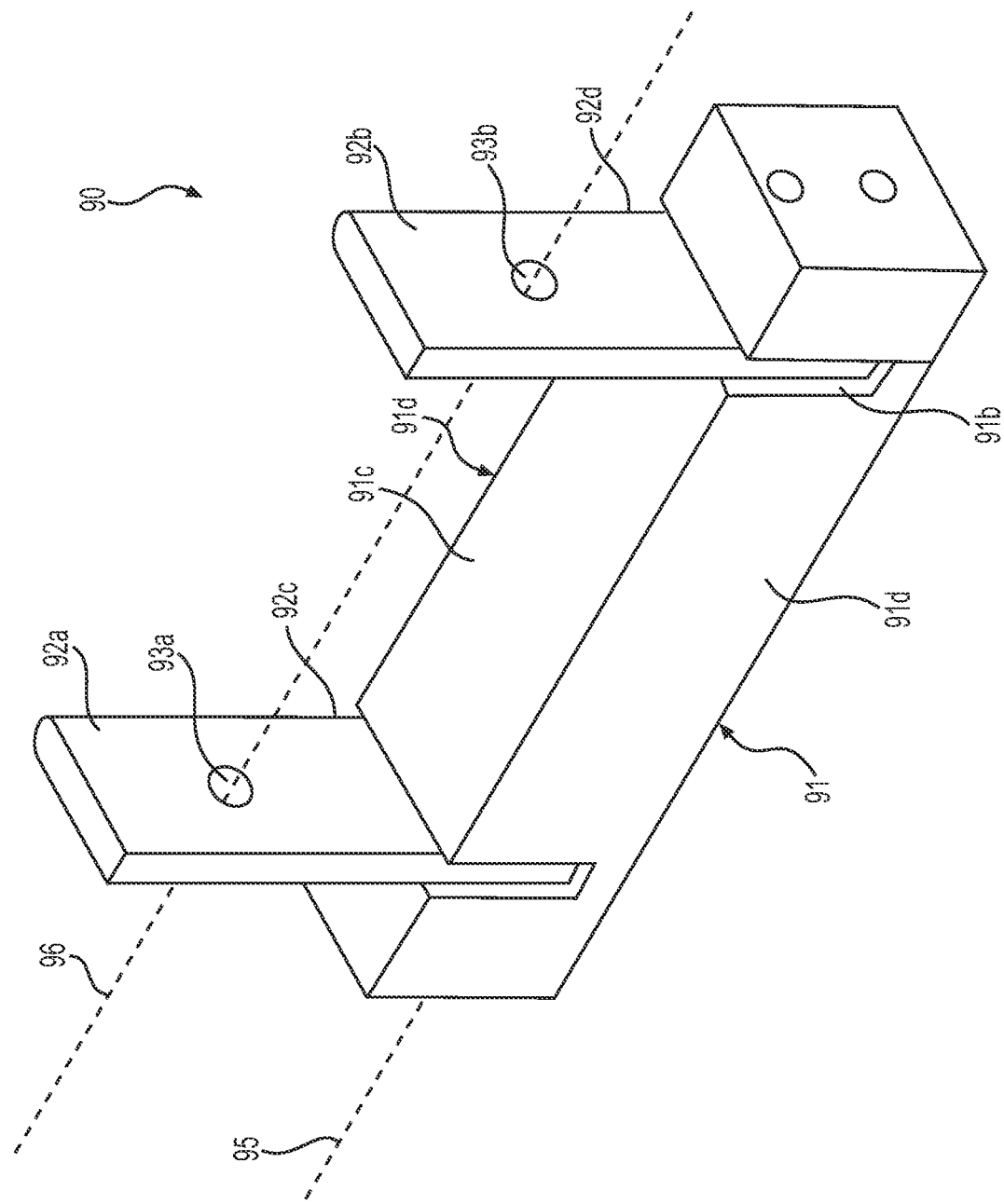
FIG. 2 is a perspective view of an alignment device according to an exemplary embodiment.

According to an exemplary embodiment, an alignment device 90, illustrated in FIG. 2, may be used to assist in the alignment of the medical laser system 1. As shown in FIG. 2, the alignment device 90 includes a body 91 extending along a longitudinal axis 95. Body 91 includes a top surface 91c, side surfaces 91d, and a bottom surface (not shown) that opposes top surface 91c. Body 91 may include two slots 91a, 91b provided at opposite ends of the body 91. Slot 91 may extend through each of top surface 91c and side surfaces 91d, but not through the bottom surface of body 91. A first insert (or extrusion) 92a may be provided in the first slot 91a and a second insert (or extrusion) 92b may be provided in the second slot 91b. A fastening mechanism, such as one or more bolts 93, may be used to fasten the first insert 92a and the second insert 92b to the body 91. It will be understood that the fastening mechanism is not limited to a bolt or a screw. Indeed, any fastening may be used, such as an adhesive or other fastening mechanism known in the art. Moreover, the body 91 may be provided without the slots 91a, 91b and the first insert 92a and the second insert 92b may be fastened to a same face of the body 91 by any mechanism known to one of skill in the art.

According to an exemplary embodiment, the first insert 92a and the second insert 92b may each include a groove 92c, 92d, respectively. The grooves 92c, 92d may cooperate with a tab (not shown) in each of the slots 91a, 91b to properly align the first insert 92a and the second insert 92b in the first slot 91a and the second slot 91b, respectively. The tabs may extend into slots 91a and 91b, first insert 92a and second insert 92b may slide along the respective tabs in a track-type arrangement.

As shown in FIG. 2, a first pinhole 93a may be provided through the first insert 92a and a second pinhole 93b may be provided through the second insert 92b. The position of the pinholes 93a, 93b on each of the protrusions 92a, 92b is not limited; however, when the protrusions 92a, 92b are attached to the body 91, a laser light should be capable of passing through each of the pinholes 93a, 93b. According to an exemplary embodiment, the pinholes 93a, 93b are located at a same position on the first insert 92a and the second insert 92b, respectively. In one embodiment, first insert 92a and second insert 92b may be substantially identical and interchangeable within alignment device 90. When first insert 92a and second insert 92b are coupled to body 91, a longitudinal optical axis 96 may extend through substantially similar positions within first insert 92a and second insert 92b. Longitudinal optical axis 96 may be substantially parallel to longitudinal axis 95. As will be explained in detail herein, this positioning of the pinholes 93a, 93b may allow an alignment laser light to pass from the output of the medical laser system 1 to the Galvo mirror 30, the relay mirrors 20a-20d, and the cavities 10a-10d to assist in the alignment of the medical laser system 1.

Figure 3:
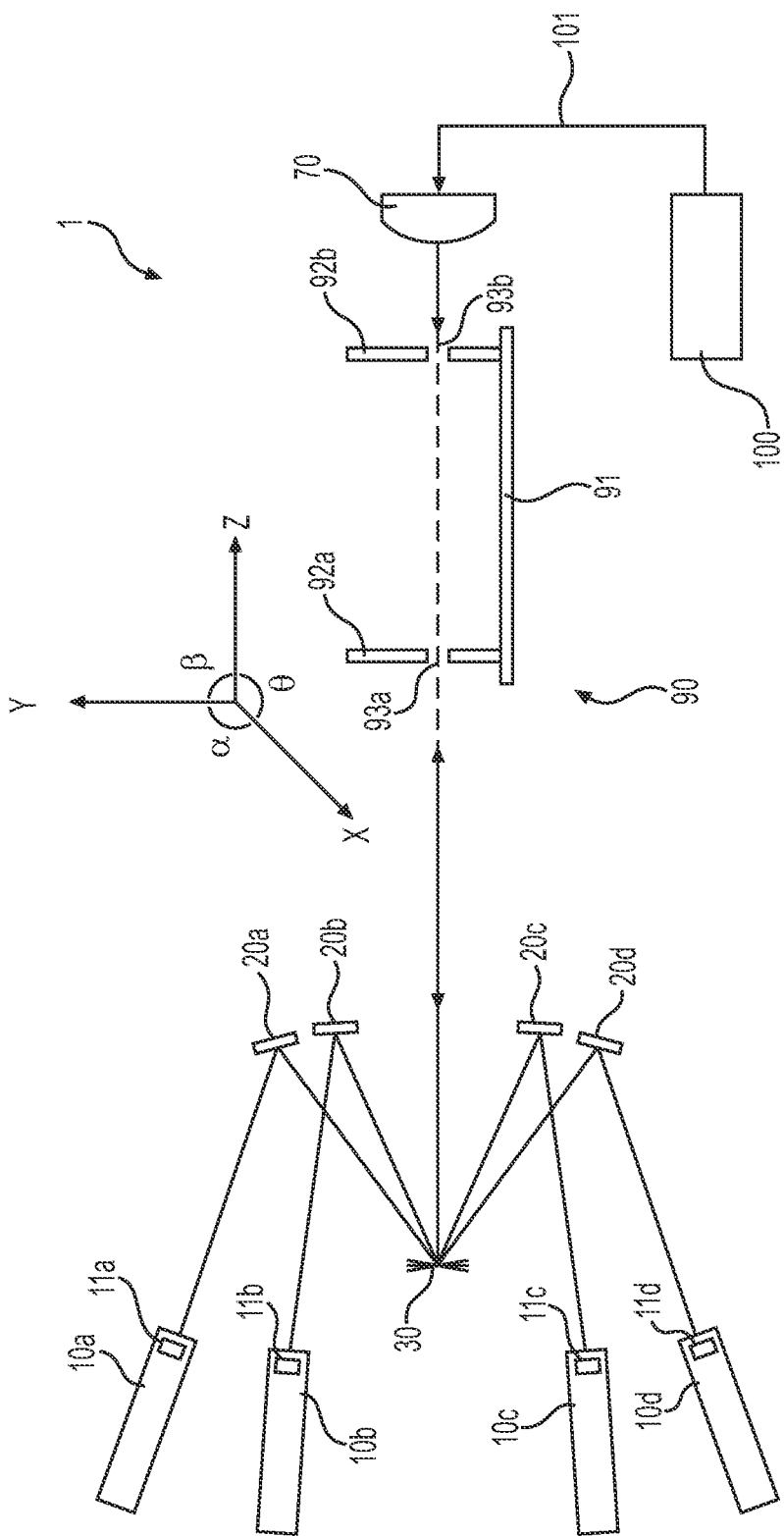
FIG. 3 is a schematic of the medical laser system of FIG. 1, in a first alignment configuration.

According to an exemplary embodiment, FIG. 3 illustrates that the alignment device 90 may be used in the medical laser system 1 to aid in the alignment thereof, in a first alignment configuration of system 1. As shown in FIG. 3, the alignment device 90 may be positioned such that the first insert 92a is provided at a location of the beam splitter 40 and the second insert 92b is provided at a location of the beam combiner 60. According to this exemplary embodiment, the beam splitter 40, the shutter 50, and the beam combiner 60 may be removed prior to inserting the alignment device 90 into the medical laser system 1. Using an alignment device 90 sized such that the first and second protrusions 92a, 92b are provided at the location of the beam splitter 40 and the beam combiner 60 may allow the user to attach the alignment device 90 in the medical laser system 1 using the same fastening elements (not shown) as used to position the beam splitter 40 and the beam combiner 60 in the medical laser system 1. It will be understood, however, that fastening the alignment device 90 is not limited and any attachment mechanism, such as thumb screws, clamps, or any other fastening mechanism not to one of ordinary skill in the art, may be used to removably fasten the alignment device 90 in the medical laser system 1 during alignment thereof. It will be understood that, after alignment of the medical laser system 1, the alignment device 90 may be removed from the medical laser system 1, and the beam splitter 40, the shutter 50, and the beam combiner 60 may be replaced and fastened in the medical laser system 1.

According to an exemplary embodiment, the relay mirrors 20a-20d may each be provided with a coating to increase the brightness of an alignment beam (alignment laser light) on an output coupling (OC) mirror 11a-11d in each of the cavities 10a-10d. The coating may provide a reflection of greater than approximately 50% at an alignment laser wavelength. Further, a thin film may be applied to enhance the brightness of the alignment beam on the OC mirrors 11a-11d. According to an exemplary embodiment, the coating may provide a reflectivity from the OC mirrors 11a-11d of greater than approximately 50%, when providing an alignment laser beam at a visible wavelength range, and an incident angle of the OC mirrors 11a-11d at 0°. In response, a single alignment beam having a size approximately 1.5 mm to 2.5 mm, or about 2 mm, in diameter may be obtained on each of the OC mirrors 11a-11d, which may simplify the alignment procedure and help ensure a more accurate alignment.

With continued reference to FIG. 3, an alignment beam source 100 may be used to provide an alignment laser beam to align the medical laser system 1. The alignment beam source 100 may include a semiconductor laser diode and a single mode optical fiber (alignment laser fiber) 101 having a core diameter of 6 µm and NA=0.12. The alignment beam source 100 according to the exemplary embodiment may provide a beam diameter of about 2.5 mm to 3.5 mm, or approximately 3 mm on the Galvo mirror 30, and a beam diameter of about 2.5 mm to 3.5 mm, or approximately 2 mm on each of the OC mirrors 11a-11d, thereby improving the alignment accuracy. It will be understood that the alignment beam source 100 is not limited to these parameters and may change according to the requirements of the laser medical system 1.

Figure 6:
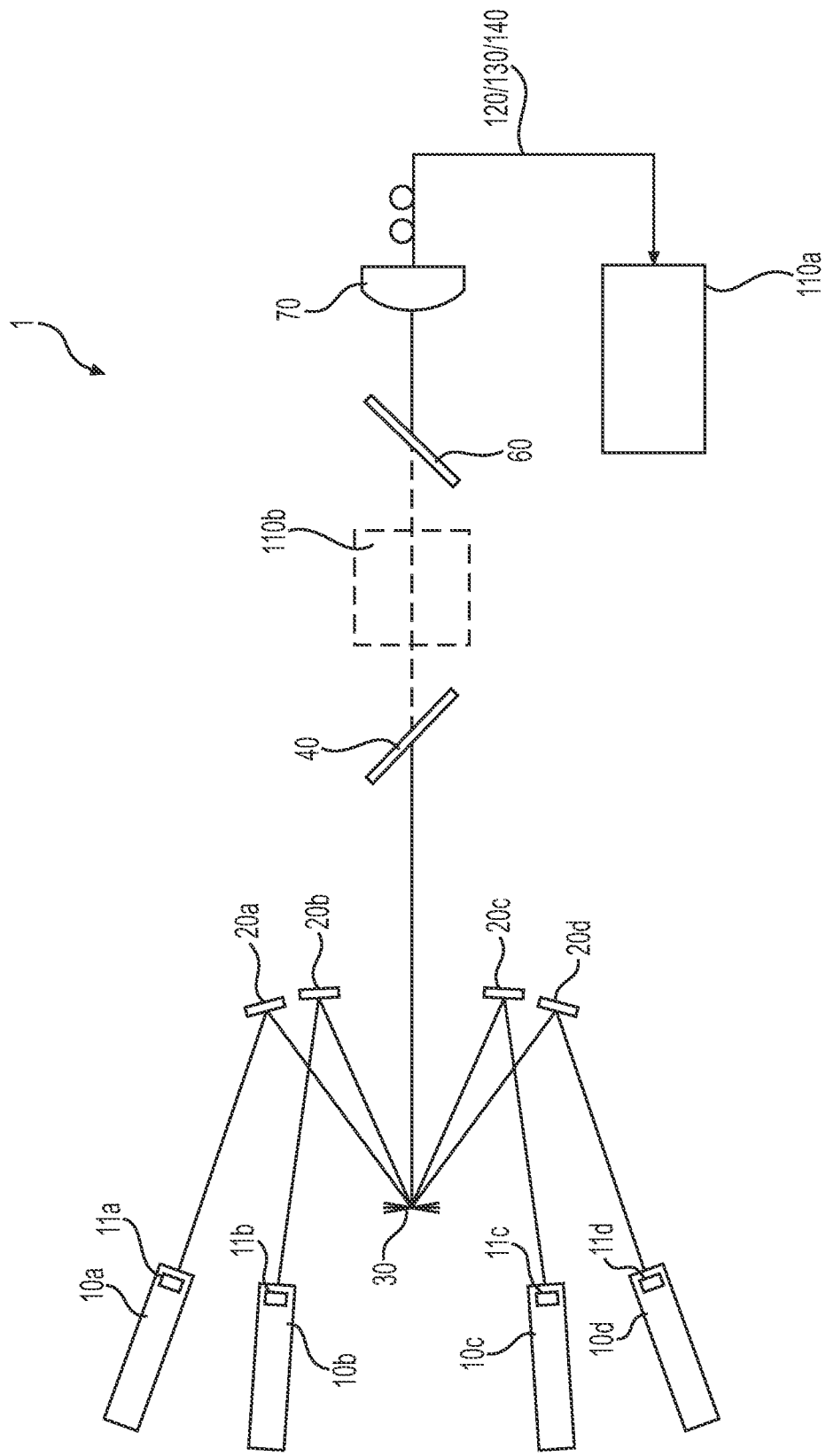
FIG. 6 is a schematic of the medical laser system of FIG. 1, in a second alignment configuration.

As further illustrated in FIG. 3, alignment laser fiber 101 of the alignment beam source 100 is connected to an output 1a of the medical laser system 1 and the alignment beam source 100. A simplified illustration of the medical laser system 1 and the alignment beam source 100 is shown in FIG. 6. The output 1a of the medical laser system 1 may be an SMA fiber connector provided after the coupling lens 70 (relative to the beam path). The output 1a is not limited to the SMA fiber connector and may be any connector suitable for outputting and receiving a laser energy.

In a second alignment configuration of system 1, shown in FIG. 6, first core fiber (test fiber) 120, which may have a diameter greater than 550 µm, may be attached to the output 1a using, for example, an SMG connector. A second core fiber 130 having a diameter of 365 µm may also be attached to the output 1a using the SMG connector. In addition, a first power meter 110a may be attached to an end of the first core fiber 120 opposite the end connected to the output 1a, as shown in FIG. 6. The optical power measured at a distal end of the fiber using first power meter 110a is measured as P1. A second power meter 110b may be provided between the beam splitter 40 and the beam combiner 60, as illustrated in FIG. 6. The optical power measured at a location proximal of the fiber is measured by the second power meter as P2. The fiber coupling efficiency is defined as P1/P2 multiplied by 100%.

The medical laser system 1 provides a reflection of the alignment laser beam from each of the OC mirrors 11a-11d when an incident angle of the OC mirrors 11a-11d is set to 0°. This orientation may provide a reflection of 35%-45%, and in some cases approximately 40%, of the alignment laser beam from the OC mirrors 11a-11d. According to an exemplary embodiment, the wavelength of the alignment laser beam may be about 625 nm to 675 nm, or 640 nm to 660 nm, and in some embodiments approximately 650 nm. It will be understood that the wavelength of the alignment laser beam is not limited thereto and any visible wavelength suitable for use for an alignment laser beam may be used.

A method of aligning the medical laser system 1 according to an exemplary embodiment will now be described. At the outset, coordinates of various elements of the medical laser system are described herein, reference for which should be made to FIG. 3.

Figure 4:
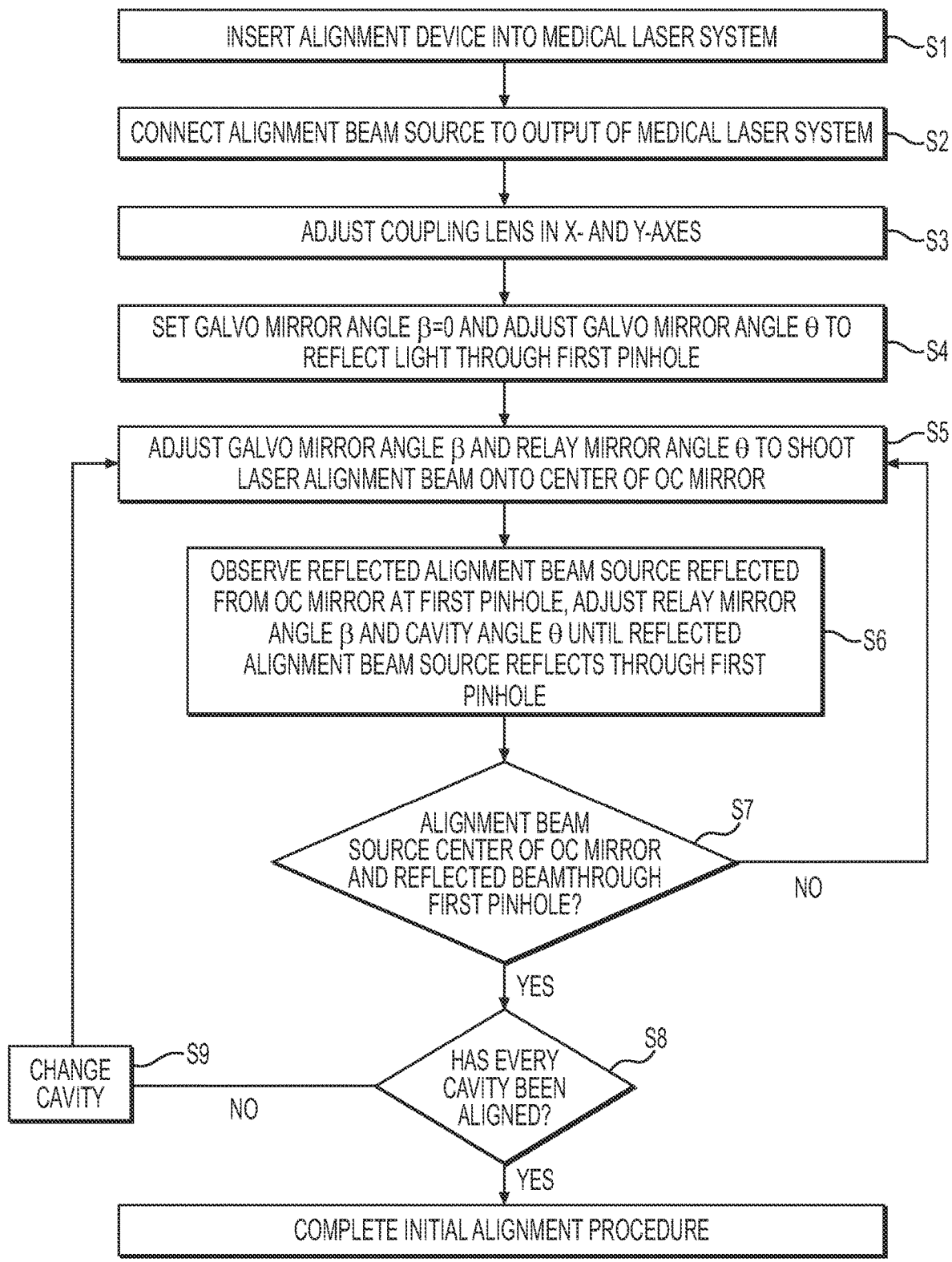
FIG. 4 is a flow chart of a first alignment procedure according to an exemplary embodiment.

FIG. 4 illustrates a flow chart of a first (e.g., initial) alignment procedure according to an exemplary embodiment. As shown in Step S1, the alignment device 90 is inserted into the medical laser system 1 between the Galvo mirror 30 and the coupling lens 70 (after beam splitter 40 and beam combiner 60 have been removed). As provided above, the alignment device 90 may be removably attached to the medical laser system 1 using the same attachment mechanism as used for attaching the beam splitter 40 and the beam combiner 60. Further, the first insert 92a may be placed in a same position as the attachment location for the beam splitter 40 and the second insert 92b may be placed in a same position as the attachment location for the beam combiner 60. For ease of understanding, the discussion will refer to the first insert 92a as being adjacent the Galvo mirror 30 and the second insert 92b as being adjacent the coupling lens 70. However, the medical laser system 1 is not limited to this orientation.

Once the alignment device 90 is inserted into the medical laser system 1, the alignment laser fiber 101 of the alignment beam source 100 is connected to the output 1a of the medical laser system 1 and the alignment beam source 100 is activated, as shown in Step S2.

In Step S3, the coupling lens 70 illustrated in FIG. 3 is adjusted in the X- and Y-axes to direct the alignment laser beam through the pinholes 93a, 93b of the first insert 92a and the second insert 92b, respectively.

In Step S4, the Galvo mirror 30 illustrated in FIG. 3 has an angle $\beta=0°$ and the angle $\theta$ of the Galvo mirror 30 is adjusted to reflect the laser alignment beam from the Galvo mirror 30 back into at least pinhole 93a of the first insert 92a. For reference purposes, a z-axis lies along the output path of the output beam; a y-axis is perpendicular to the z-axis and extends in a vertical direction in FIG. 1, e.g., perpendicular to a base plate (not shown) on which Galvo mirror 30 and relay mirrors 20a-d are disposed; and a x-axis is perpendicular to both the z-axis and the y-axis and is normal to FIG. 1. The angle $\beta$ may be defined as a rotation angle along a plane defined by the x- and z-axes, e.g., a rotation of Galvo mirror 30 and/or relay mirrors 20a-d in a horizontal direction, whereas the angle $\theta$ may be defined as a rotation angle along a plane defined by the y- and z-axes, e.g. a rotation of Galvo mirror 30 and/or relay mirrors 20a-d in a vertical direction.

Once the laser alignment beam is reflected back into at least pinhole 93a of the first insert 92a, Step S5 is performed. In Step S5, the angle $\beta$ of the Galvo mirror 30 and the angle $\theta$ of a first relay mirror 20a are adjusted to direct the laser alignment beam onto the center of a first OC mirror 11a of a first cavity 10a.

In Step S6, a lens paper is placed over the pinhole 93a on a side of the first insert 92a facing the first OC mirror 11a. The lens paper is used to observe the laser alignment beam reflected from the first OC mirror 11a around the pinhole 93a of the alignment device 90. During Step S6, the angle $\beta$ of the first relay mirror 20a and the angle $\theta$ of the cavity 10a are adjusted until the laser alignment beam is reflected back through the first pinhole 93a of the alignment device 90.

It is possible that, after Steps S5 and S6, the laser alignment beam is not on the center of the first OC mirror 11a and the laser alignment beam reflected from the first OC mirror 11a is not reflected through the first pinhole 93a. In the event that this occurs, Step S7 includes repeating Steps S5 and S6 until the laser alignment beam is on the center of the first OC mirror 11a and the laser alignment beam reflected from the first OC mirror 11a is reflected through the first pinhole 93a. A lens paper is placed in front of OC mirror 11a to determine if the alignment beam in on the center of the OC mirror 11a.

Once the laser alignment beam is on the center, or at least substantially on the center, of the first OC mirror 11a and the laser alignment beam reflected from the first OC mirror 11a is reflected through the first pinhole 93a, it is determined in Step S8 whether all cavities 10a-10d have been aligned. If not, in Step S9 the next cavity is selected and Steps S5 to S7 are repeated for each cavity 10b-10d using corresponding relay mirrors 20b-20d and the Galvo mirror 30.

Figure 5A:
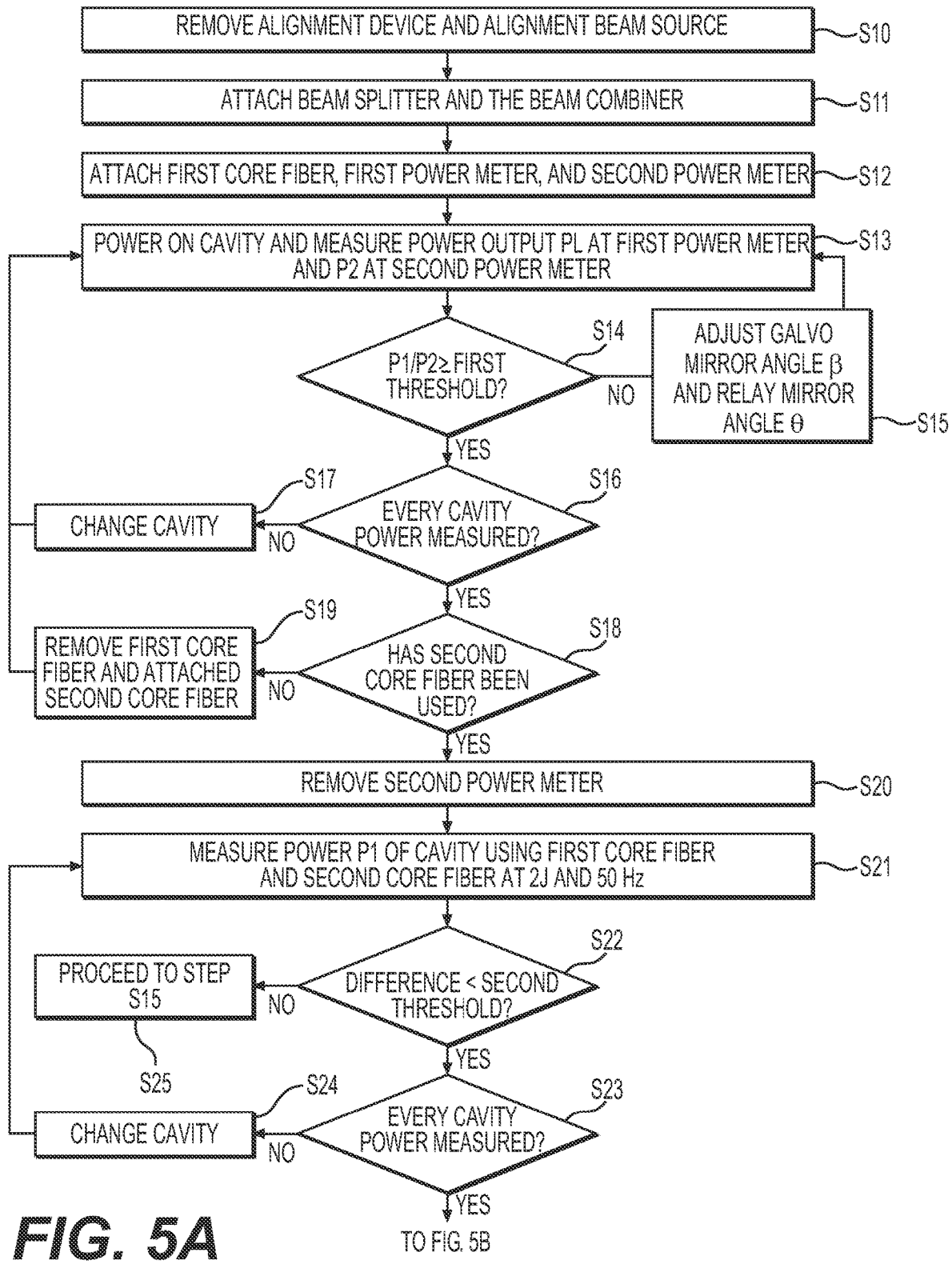
FIGS. 5A and 5B are flow charts of a second alignment procedure according to an exemplary embodiment.
Figure 5B:
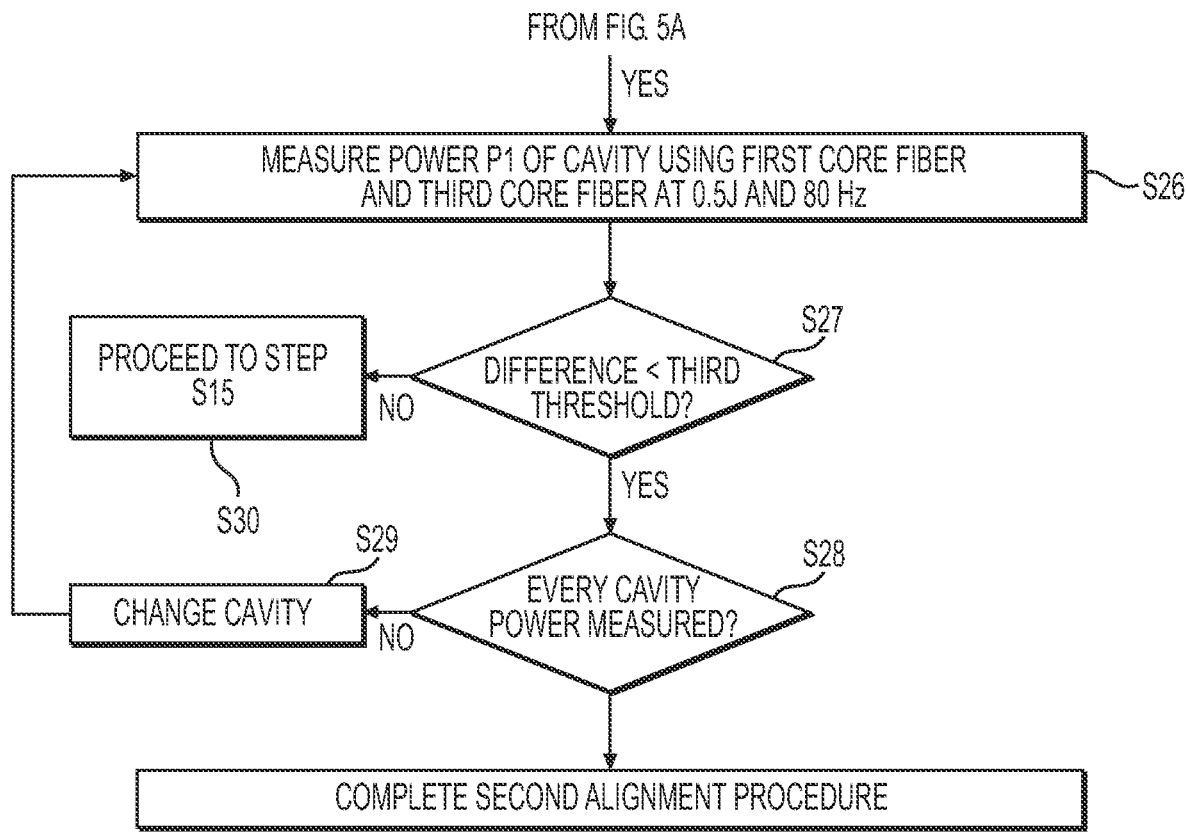

Once the first alignment procedure is completed, a second (e.g., final) alignment procedure is performed, as illustrated in FIGS. 5A and 5B.

As illustrated in FIGS. 5A and 5B, the alignment beam source 100 and the alignment device 90 are removed from the medical laser system 1 in Step S10.

In Step S11, the beam splitter 40 and the beam combiner 60 are placed into the medical laser system 1 in the positions shown in FIG. 6. The beam splitter 40 and the beam combiner 60 may be attached to the medical laser system 1 using the same or different fastening mechanisms as those used to removably fasten the alignment device 90.

In Step S12, the first core fiber 120 may be attached to the output 1a using an SMG connector. In addition, the first power meter 110a may be attached to an end of the first core fiber 120 opposite the end connected to the output 1a. A second power meter 110b may be provided between the beam splitter 40 and the beam combiner 60.

During Step S13, the first cavity 10a may be powered on and the pulse energy is gradually increased from 0.2 J to 0.5 J. During this time, a power P1 is measured at the first power meter 110a and a power P2 is measured at the second power meter 110b at different pulse energies. The pulse energies may be preset and the number of pulse energies at which P1 and P2 measurements are performed is not limited.

In Step S14, it is determined whether P1/P2 is greater than or equal to a first threshold value (e.g., 80%). If P1/P2 is less than 80%, Step S15 is performed, in which the angle $\beta$ of the Galvo mirror 30 and the angle $\theta$ of the relay mirror 20a is adjusted. The adjustment of the Galvo mirror 30 and the relay mirror 20a is iterative until the ratio P1/P2 is greater than or equal to the first threshold value. After Step S15 is performed, Step S13 is repeated to determine whether P1/P2 is greater than or equal to the first threshold value. According to some embodiments, the first threshold may be determined by a specification of medical laser system 1, e.g., a tolerance of the system. Additionally or alternatively, the first threshold fiber coupling efficiency may account for transmission loss of the beam combiner, the fiber coupling lens 70, and a blast shield; a reflection lows of two surfaces of the fiber; absorption by the fiber and scattering loss; and/or a coupling loss.

Once it is determined that P1/P2 is greater than or equal to the first threshold value, Step S16 determines if the power of each cavity has been tested. If the power of each cavity has not been measured, the cavity is changed in Step S17. Steps S13-S15 are thus performed for each of cavities 10b-10d. While the medical laser system 1 described herein includes four cavities 10a-10d, the medical laser system 1 is not limited thereto. Accordingly, Steps S13-S15 should be performed for each cavity of the medical laser system 1.

After Steps S13-S15 are completed for each of cavities 10a-10d, Step S18 is performed, which determined if a second core fiber (test fiber) 130 has been used. If the second core fiber 130 has not yet been used, the first core fiber 120, which may have a diameter of 910 μm, is replaced with a second core fiber 130 having a diameter of 365 μm in Step 19. Steps S13-S17 are repeated using the second core fiber 130. The second core fiber 130 represents a fiber which may be used in medical laser system 1, since a 100 watt laser may be coupled into a fiber having a diameter of 365 μm. Thus, this tests to ensure proper orientation when using a fiber specified for use with medical laser system 1.

After the power of each of cavities 10a-10d has been measured using the first core fiber 120 and the second core fiber 130, Step S20 is performed, during which the second power meter 110b is removed from the medical laser system 1.

Step S21 includes measuring the power P1 of the pulse from the first cavity 10a using the first power meter 110a using the first core fiber 120 and the second core fiber 130. The first cavity 10a is set to produce a beam having an energy of up to about 2 J per pulse at about 25-75 Hz, or about 50 Hz in some embodiments. If the difference in output power P1 at the first power meter 110a between the first core fiber 120 and the second core fiber 130 is less than a second threshold value (e.g. 5%) in Step S22, Step S21 is complete. If the difference in the output power P1 is greater than the second threshold value, Step S25 is performed, in which the method proceeds back to Step S15 such that Galvo mirror 30 and relay mirror 20a are readjusted.

In Step S23, it is determined whether the power P1 of each of cavities 10a-10d has been measured. If not, the cavity is changed in S24 and Steps S21 and S22 are repeated for each of the cavities 10b-10d.

Step S26 includes measuring the power P1 of the first cavity 10a using the first power meter 110a using the first core fiber 120 and a third core fiber (test fiber) 140 having a diameter of 242 μm and NA=0.28. The first cavity 10a is set to produce a beam having an energy of 0.5 J per pulse at 80 Hz. If the difference in output power P1 at the first power meter 110a between the first core fiber 120 and the third core fiber 140 is less than a third threshold value (e.g., 10%) in Step S27, Step S26 is complete. If the difference in the output power P1 in Step S26 is greater than the third threshold value, Step S30 is performed, in which the method proceeds back to Step S15 such that Galvo mirror 30 and relay mirror 20a are readjusted.

In Step S28, it is determined whether the power P1 of each of cavities 10a-10d has been measured. If not, the cavity is changed in S29 and Steps S26 and S27 are repeated for each of the cavities 10b-10d.

According to an exemplary embodiment, the alignment method described herein may be performed using two phases, thereby eliminating the need for a third phase. According to an embodiment, the system can be provided without a light emitting diode (LED), since an LED produces a beam that is insufficient to use in aligning the medical laser system. According to another embodiment, the system may be used without a thermal paper, since the alignment beam source may be seen directly on an insert. According to yet another exemplary embodiment, the alignment system and method described herein may be used without the need for a special beam splitter, e.g., a beam splitter that reflects more light to a power meter than coupled into a fiber at the output of the system. Moreover, the alignment system and method described herein may be used without the need for thermal paper.

The alignment procedure described above may significantly reduce the alignment time of the medical laser system 1. Due to the smaller and brighter alignment beam from the alignment beam source 100 and the alignment device 90, the alignment procedure described herein is more accurate, simpler, and less time consuming than conventional techniques. The reflection beam from the OC mirrors 11a-11d through the first pinhole 93a is advantageous in that it ensures that the output laser beam is on the same optical axis of the output fiber 80 attached to the output 1a of the medical laser system 1. Accordingly, after the alignment using the alignment beam source 100, few if any fine-alignments of the medical laser system 1 are required to finalize the alignment. The alignment procedures of the present disclosure also may help technicians and operators service laser systems in the field, without requiring the systems to be sent off-site for service.

It will be understood that reference is made to a number of cavities and/or mirrors in the medical laser system 1. It will be understood that the devices are not limited to this number and may change according to the requirement of the medical laser system 1. Further, while reference is made to a medical/surgical laser system, the alignment technique described herein is not limited to a medical/surgical laser system and may be used with any laser system.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for aligning a laser system, the method comprising:
   activating a laser cavity of the laser system to emit a first laser light, wherein the first laser light is emitted along a first path toward a first mirror of the laser system and diverted along a second path from the first mirror through a first output fiber coupled to the laser system;
   measuring a first power of the first laser light at the first output fiber;
   measuring a second power of a reflection of the first laser light between a beam splitter and a beam combiner of the laser system;
   determining a first ratio of the first power of the first laser light to the second power of the reflection of the first laser light; and
   adjusting a position of the first mirror until the first ratio is below a first threshold, while the first output fiber is coupled to the laser system.

2. The method of claim 1, wherein the first laser light is further diverted along a third path, different than the first path and the second path, from the first mirror to a second mirror of the laser system, and the method further comprises:
   adjusting positions of the first mirror and the second mirror until the first ratio is below the first threshold, while the first output fiber is coupled to the laser system.

3. The method of claim 1, further comprising:
   replacing the first output fiber with a second output fiber having one or more different optical properties than the first output fiber;
   activating the laser cavity to emit a second laser light, wherein the second laser light is emitted along the first path toward the first mirror and diverted along the second path from the first mirror through the second output fiber;
   measuring a first power of the second laser light at the second output fiber;
   measuring a second power of a reflection of the second laser light between the beam splitter and the beam combiner;

determining a second ratio of the first power of the second laser light to the second power of the reflection of the second laser light; and adjusting a position of the first mirror until the second ratio is below the first threshold, while the second output fiber is coupled to the laser system.

4. The method of claim 3, wherein the second laser light is further diverted along a third path, different than the first path and the second path, from the first mirror to a second mirror of the laser system, and the method further comprises:

adjusting positions of the first mirror and the second mirror until the second ratio is below the first threshold, while the second output fiber is coupled to the laser system.

5. The method of claim 1, further comprising:

while the first output fiber is coupled to the laser system:
  activating the laser cavity to emit a third laser light, wherein the third laser light is emitted along the first path toward the first mirror and diverted along the second path from the first mirror through the first output fiber; and
  measuring a first power of the third laser light at the first output fiber;

replacing the first output fiber with a second output fiber having one or more different optical properties than the first output fiber, and while the second output fiber is coupled to the laser system:
  activating the laser cavity to emit a fourth laser light, wherein the fourth laser light is emitted along the first path toward the first mirror and diverted along the second path from the first mirror through the second output fiber; and
  measuring a first power of the fourth laser light at the second output fiber;

determining whether a difference in the first power of the third laser light and the fourth laser light is less than a second threshold; and adjusting a position of the first mirror until the difference is less than the second threshold.

6. The method of claim 5, wherein, while each of the first output fiber and the second output fiber is respectively coupled to the laser system, the third laser light and the fourth laser light are respectively further diverted along a third path, different than the first path and the second path, from the first mirror to a second mirror of the laser system, and the method further comprises:

adjusting positions of the first mirror and the second mirror until the difference is less than the second threshold.

7. The method of claim 1, further comprising:

while the first output fiber is coupled to the laser system:
  activating the laser cavity to emit a fifth laser light, wherein the fifth laser light is emitted along the first path toward the first mirror and diverted along the second path from the first mirror through the first output fiber; and
  measuring a first power of the fifth laser light at the first output fiber;

replacing the first output fiber with a third output fiber having one or more different optical properties than the first output fiber, and while the third output fiber is coupled to the laser system:
  activating the laser cavity to emit a sixth laser light, wherein the sixth laser light is emitted along the first path toward the first mirror and diverted along the second path from the first mirror through the third output fiber; and
  measuring a first power of the sixth laser light at the third output fiber;

determining whether a difference in the first power of the fifth laser light and the sixth laser light is less than a third threshold; and adjusting a position of the first mirror until the difference is less than the third threshold.

8. The method of claim 7, wherein, while the first output fiber and the third output fiber are each coupled to the laser system, the fifth laser light and the sixth laser light are respectively further diverted along a third path, different than the first path and the second path, from the first mirror to a second mirror of the laser system, and the method further comprises:

adjusting positions of the first mirror and the second mirror until the difference is less than the third threshold.

9. A system for aligning a laser system, the system comprising:

a first output fiber removably connected to the laser system at a first end of the first output fiber;

a first power meter removably connected to a second end of the first output fiber opposite the first end and configured to measure a first power of a first laser light emitted from a laser cavity of the laser system, at the first output fiber, wherein the first laser light is emitted along a first path toward a first mirror and diverted along a second path different from the first path from the first mirror through the first output fiber; and a second power meter removably located between a beam splitter and a beam combiner of the laser system and configured to measure a second power of a reflection of the first laser light between the beam splitter and the beam combiner, wherein a position of the first mirror is adjusted until a first ratio of the first power of the first laser light to the second power of the reflection of the first laser light is below a first threshold.

10. The system of claim 9, wherein the first laser light is further diverted along a third path, different than the first path and the second path, from the first mirror to a second mirror of the laser system, and positions of the first mirror and the second mirror are adjusted until the first ratio is below the first threshold.

11. The system of claim 9, further comprising a second output fiber having one or more different optical properties than the first output fiber, wherein the first output fiber is replaceable with the second output fiber in the system.

12. The system of claim 11, wherein:

the first output fiber is replaced with the second output fiber, the first power meter is further configured to measure a first power of a second laser light emitted from the laser cavity, at the second output fiber, the second power meter is further configured to measure a second power of a reflection of the second laser light between the beam splitter and the beam combiner, and the position of the first mirror is adjusted until a second ratio of the first power of the second laser light to the second power of the reflection of the second laser light is below the first threshold, while the second output fiber is coupled to the laser system.

13. The system of claim 12, wherein the second laser light is further diverted along a third path, different than the first path and the second path, from the first mirror to a second mirror of the laser system, and positions of the first mirror and the second mirror are adjusted until the second ratio is below the first threshold.

14. The system of claim 11, wherein:
the second power meter is removed from the system,
the first power meter is further configured to measure a first power of a third laser light emitted from the laser cavity, at the first output fiber, while the first output fiber is connected to the laser system,
the first output fiber is replaced by the second output fiber, the first power meter is further configured to measure a first power of a fourth laser light emitted from the laser cavity, at the second output fiber, while the second output fiber is connected to the laser system, and
the position of the first mirror is adjusted until a difference in the third laser light and the fourth laser light is less than a second threshold.

15. The system of claim 14, wherein each of the third laser light and the fourth laser light is further diverted along a third path, different than the first path and the second path, from the first mirror to a second mirror of the laser system, and positions of the first mirror and the second mirror are adjusted until the difference is less than the second threshold.

16. The system of claim 9, further comprising a third output fiber having one or more different optical properties than the first output fiber, wherein the first output fiber is replaceable with the third output fiber in the system.

17. The system of claim 16, wherein:
the first power meter is further configured to measure a first power of a fifth laser light emitted from the laser cavity, at the first output fiber, while the first output fiber is connected to the laser system,
the first output fiber is replaced by the third output fiber,
the first power meter is further configured to measure a first power of a sixth laser light emitted from the laser cavity, at the third output fiber, while the third output fiber is connected to the laser system, and
the position of the first mirror is adjusted until a difference in the first power of the fifth laser light and the sixth laser light is less than a third threshold.

18. The system of claim 17, wherein each of the fifth laser light and the sixth laser light is further diverted along a third path, different than the first path and the second path, from the first mirror to a second mirror of the laser system, and positions of the first mirror and the second mirror are adjusted until the difference is less than the third threshold.

19. A method for aligning a laser system, the method comprising:
activating a laser cavity of the laser system to emit a first laser light, wherein the first laser light is emitted along a first path toward a first mirror of the laser system, diverted along a second path, different than the first path, from the first mirror to a second mirror, and further diverted along a third path, different than the first path and the second path, from the second mirror through a first output fiber;
measuring a first power of the first laser light at the first output fiber;
measuring a second power of a reflection of the first laser light between a beam splitter and a beam combiner;
determining a first ratio of the first power of the first laser light to the second power of the reflection of the first laser light; and
adjusting positions of the first mirror and/or the second mirror until the first ratio is below a first threshold, while the first output fiber is coupled to the laser system.

20. The method of claim 19, further comprising:
replacing the first output fiber with a second output fiber having one or more different optical properties than the first output fiber;
activating the laser cavity to emit a second laser light, wherein the second laser light is emitted along the first path toward the first mirror, diverted along the second path from the first mirror to the second mirror, and further diverted along the third path from the second mirror through the second output fiber;
measuring a first power of the second laser light at the second output fiber;
measuring a second power of a reflection of the second laser light between the beam splitter and the beam combiner; and
adjusting positions of the first mirror and/or the second mirror until a second ratio of the first power of the second laser light to the second power of the reflection of the second laser light is below the first threshold, while the second output fiber is coupled to the laser system.

* * * * *